United States Patent
Cabri et al.

(10) Patent No.: US 8,269,007 B2
(45) Date of Patent: Sep. 18, 2012

(54) CRYSTALLINE FORM II OF 7-(DIMETHOXY-METHYL) CAMPTOTHECIN, ITS USE AS INTERMEDIATE AND PRODUCTS OBTAINED THEREFROM

(75) Inventors: Walter Cabri, Rozzano (IT); Mauro Marzi, Rome (IT); Fabrizio Giorgi, Ardea (IT); Elena Badaloni, Rome (IT); Silvia Armaroli, Gallo Poggio Renatico (IT); Giuseppe Marazzi, Milan (IT)

(73) Assignee: Sigma-Tau Industrie Farmaceutiche Riunite SpA, Rome (IT)

( * ) Notice: Subject to any disclaimer, the term of this patent is extended or adjusted under 35 U.S.C. 154(b) by 279 days.

(21) Appl. No.: 12/670,905

(22) PCT Filed: Jul. 22, 2008

(86) PCT No.: PCT/EP2008/059597
§ 371 (c)(1),
(2), (4) Date: Mar. 3, 2010

(87) PCT Pub. No.: WO2009/016068
PCT Pub. Date: Feb. 5, 2009

(65) Prior Publication Data
US 2010/0249414 A1    Sep. 30, 2010

(30) Foreign Application Priority Data
Aug. 1, 2007 (EP) ..................... 07113597

(51) Int. Cl.
*C07D 491/22* (2006.01)
*C07D 491/147* (2006.01)
(52) U.S. Cl. ........................................... 546/48; 546/47
(58) Field of Classification Search ................... 546/48, 546/47
See application file for complete search history.

(56) References Cited

FOREIGN PATENT DOCUMENTS
EP    0 056 692    7/1982
WO    03/101995    12/2003

OTHER PUBLICATIONS

Sawada, S. et al., "Chemical Modification of an Antitumor Alkaloid Camptothecin: Synthesis and Antitumor Activity of 7-C-Substituted Camptothecins" Chemical and Pharmaceutical Bulletin, vol. 39, No. 10, Oct. 1991, pp. 2574-2580.

*Primary Examiner* — Charanjit Aulakh
(74) *Attorney, Agent, or Firm* — Lucas & Mercanti, LLP (57) ABSTRACT

This invention relates to a process for preparing a crystalline form of (4S)-11(dimethoxymethyl)-4-ethyl-4-hydroxy-1H-pyrano[3'4':6,7]indolizino[1,2-b]quinoline-3,14(4H,12H)-dione, also named 7-(dimethoxy-methyl)camptothecin). With the provision of a particular crystallization step, in appropriate way, a new crystalline form of the above compound is obtained. The process for the preparation of the polymorph Form II comprises transforming camptothecin to the corresponding 7-(dimethoxy-methyl)-camptothecin, and crystallizing from methanol.

15 Claims, 8 Drawing Sheets

CRYSTALLINE FORM II OF 7-(DIMETHOXY-METHYL) CAMPTOTHECIN, ITS USE AS INTERMEDIATE AND PRODUCTS OBTAINED THEREFROM

This application is a 35 U.S.C. §371 national phase of PCT/EP2008/059597 filed on Jul. 22, 2008, which claims priority to and the benefit of European Application No. 07113597.4 filed on Aug. 1, 2007, the contents of which are incorporated herein by reference.

The present invention relates to the field of organic chemistry, in particular to compounds useful as intermediates in processes for the preparation of active ingredients in medicine.

FIELD OF THE INVENTION

This invention relates to a process for preparing a crystalline form of (4S)-11-(dimethoxymethyl)-4-ethyl-4-hydroxy-1H-pyrano[3',4':6,7]indolizino[1,2-b]qui-noline-3,14(4H,12H)-dione (CAS n 84017-99-2), also named 7-(dimethoxy-methyl)camptothecin. With the provision of a particular crystallization step, in appropriate way, a new crystalline form of the above compound is obtained.

BACKGROUND OF THE INVENTION

Camptothecin is an alkaloid, which demonstrated a wide spectrum of antitumor activity, in particular against colon tumors, other solid tumors and leukemias, and the first clinical trials were performed in the early 70's.

Since Camptothecin (CPT) has low water solubility and is rather toxic, a number of derivatives were proposed in the art in order to make available better drugs, in particular with lower toxicity and higher water solubility.

Many camptothecin derivatives were prepared and made available in the art through several synthetic routes.

The quality of the final product, such as its purity level or the easiness of isolation may depend also on the synthetic route and the kind of intermediate products.

In patent EP 1 044 977 and in Dallavalle S. et al., J. Med. Chem. 2001, 44, 3264-3274, camptothecin derivatives bearing an alkyloxime O-substituted at position 7 and endowed with antitumor activity higher than the compound of reference topotecan are described. Moreover these camptothecin derivatives bearing an imino group on position 7, also show an improved therapeutic index. One of the preferred molecules is 7-t-butoxyiminomethylcamptothecin (CPT 184) and known under the INN name Gimatecan.

7-(dimethoxy-methyl)camptothecin is disclosed in EP 0 056 692 and in Sawada, S., et al., Chemical & Pharmaceutical Bulletin (1991), 39(10), 2574-80.

This compound is used in different patents as intermediate in the synthesis of camptothecin derivatives.

7-(dimethoxy-methyl)-camptothecin can be prepared by ordinary acetalization of camptothecin 7-aldehyde, for example by heating camptothecin 7-aldehyde in hot methanol in the presence of an acid. Alternatively, this compound can be prepared in a single step by treating 7-hydroxymethyl-camptothecin with an acid in the presence of methanol, see the above mentioned EP 0 056 692.

Acetalization is an equilibrium reaction and the starting aldehyde can be present in a certain amount. Moreover, acetals can be converted in the starting aldehyde in the presence of acids.

It is well-known that aldehydes are not endowed with high stability and they tend to polymerize giving side products which are difficult to eliminate from reaction mixtures and affect the purity of the final product.

The absence of the aldehyde allows crystallization and elimination of other unwished impurities, which can be present both in the starting material and derive from the reaction. For example, 9, 10 and 11 hydroxy- and methoxy-camptothecins (see below general formula 1), mappicine (see below general formula 2), and their derivatives are side derivatives produced in the reaction of formation of 7-(dimethoxy-methyl)camptothecin.

R, R₁ = H, OH, OCH₃
R₂ = H, OCH₃
R₃ = H, CH₂OH, CHO, C(OMe)₂

R = H, CH₂OH, CHO, C(OMe)₂

WO2006/067092 discloses a stereoselective process for the preparation of crystalline forms of Gimatecan. This process allows the stereoselective preparation of Gimatecan. With the addition of further dissolution and precipitation steps carried out in appropriate different solvent mixtures, four new crystalline forms of Gimatecan are also obtainable by using the same stereoselective process.

7-(dimethoxy-methyl)camptothecin is only mentioned as starting material, with no characterization.

WO03/101995 discloses camptothecins with a modified lactone ring and 7-(dimethoxy-methyl)camptothecin is used as intermediate in the synthesis of the final products. 7-(dimethoxy-methyl)camptothecin preparation is provided as purified from column chromatography and as a yellow solid with m.p. 201° C. (dec.). Product yield is 55%.

In the above mentioned Chemical & Pharmaceutical Bulletin (1991), 39(10), 2574-80 and in EP 0 056 692, the 7-(dimethoxy-methyl)camptothecin is disclosed as purified from column, m.p. 222-224° C. (dec.) and needle crystal.

Pharmaceutical legislations are stricter and stricter on safety issues concerning drug manufacturing. One aspect is Good Manufacturing Practice (GMP, see for Example EMEA and FDA Guidelines) and a sensitive topic is represented by standardization of intermediate compounds and impurity levels.

There is still the need of a form of 7-(dimethoxy-methyl) camptothecin of higher purity and that can be used for subsequent preparation of camptothecin derivatives to be used as drugs, meeting the severe regulatory requirements easier.

From a regulatory point of view, a high purity intermediate means a higher purity final product, with more severe specifications, therefore lesser quality variability. This latter aspect is requested and appreciated by Regulatory Authorities. Moreover, crystallization of an intermediate product represents an optimal purification step, allowing a better control of final quality, thus meeting GMP requirements easier and facilitating the whole production process. In this context, WO/03101995 does not teach any crystallization.

Another, additional need in synthesis of drugs is the stability of intermediate compounds. Stability is a desirable and necessary property for the intermediate compounds, since they are able to withstand chemical reaction conditions, in particular temperatures, without undergoing degradation or decomposition. More in particular, a high melting point, especially for those compounds which melt with decomposition, is recommended, as to avoid the presence in the reaction mixture of degradation side products, which make purification of the final product (the drug) much more difficult, even impossible.

SUMMARY OF THE INVENTION

We have now surprisingly found a new form of (4S)-11-(dimethoxymethyl)-4-ethyl-4-hydroxy-1H-pyrano[3',4':6,7]indolizino[1,2-b]quinoline-3,14(4H,12H)-dione, or otherwise named in this description and claims 7-(dimethoxymethyl)camptothecin (also named Form II or with our code ST2337) which provides an improvement in the state of the art of camptothecin derivative preparation.

In particular, the present invention provides a polymorph of 7-(dimethoxy-methyl)camptothecin which is endowed with higher purity, in particular with respect to side products of aldehyde type and derivatives thereof.

Therefore, it is an object of the present invention the crystalline form of 7-(dimethoxy-methyl)camptothecin Form II.

Another object of the present invention is a process for the preparation of the above crystalline form.

A further object of the present invention is the use of the crystalline form of 7-(dimethoxy-methyl)camptothecin as intermediate in a process for the preparation of camptothecin derivatives.

These and other objects will be illustrated in detail in the foregoing description, also by means of Figures and Examples.

DETAILED DESCRIPTION OF THE INVENTION

The polymorph Form II of 7-(dimethoxy-methyl)-camptothecin of the present invention is characterized by the physico-chemical parameters provided in this description.

A particular advantage of the polymorph Form II according to the present invention is to be substantially free from aldehyde impurities and derivatives thereof.

By the term "substantially free" it is intended that the compound of the present invention contains no aldehyde impurities and derivatives thereof, or at least no detectable amounts, or at least amounts below the admitted limits stated by National or European Pharmacopoeias.

By the term "aldehyde impurities and derivatives thereof" it is intended a 7-formyl-camptothecin, said camptothecin being optionally substituted and/or having a modified lactone, an aldehyde polymer product, or any derivative of aldehyde.

The polymorph Form II of 7-(dimethoxy-methyl)camptothecin is prepared by transformation of camptothecin, through its 7-keto-derivative:

The process according to the present invention comprises the following steps:

a. oxidizing position 7 of camptothecin or a derivative thereof to obtain the corresponding 7-keto-camptothecin or 7-keto-camptothecin derivative;

b. treating 7-keto-camptothecin or 7-keto-camptothecin derivative obtained in step a) with methanol, in the presence of an acid to obtain a first, acid methanol reaction mixture;
c. neutralizing said first, acid methanol reaction mixture from step b) to give a second, substantially neutral methanol reaction mixture;
d. adding water to said second, substantially neutral methanol reaction mixture, to obtain a precipitate;
e. separating said precipitate of step d) to obtain an isolated precipitate;
f. crystallizing said isolated precipitate of step e) from methanol to give said polymorph.

The oxidizing step of step a) can be performed according to well known methods, see for example U.S. Pat. No. 6,194,579.

In a preferred embodiment of the present invention, oxidizing step is performed with a first oxidizing system and a second oxidizing system. In a further preferred embodiment, said first oxidizing system is 30% $H_2O_2$/Fe(II) salt and said second oxidizing system is selected from the group consisting of acetic acid, $CrO_3$, and $MnO_2$. In the most preferred embodiment, said first oxidizing system is 30% $H_2O_2$/iron sulphate and said second oxidizing system is manganese dioxide (see WO03/101995).

Step b) is also a well-known procedure for obtaining acetals of aldehyde compounds. In a preferred embodiment, said first, acid methanol reaction mixture is selected from the group consisting of distilled methanol and a low water methanol mixture, for example 30% water/70% methanol solution.

The acid used in step b) can be any organic or inorganic acid which does not interfere with the progress of reaction or with the stability of the starting material or of the final product. Typically, said acid is selected from the group consisting of $H_2SO_4$, $CH_3COOH$, $H_3PO_4$, HCl $SOCl_2$, $COCl_2$, $CH_3SO_2OH$, $CH_3PhSO_2OH$, $CF_3COOH$, $CF_3SO_3H$. The preferred acid is 98% $H_2SO_4$ in a concentration of 10% v/v.

Steps c), d) and e) are also carried out according to common practice and the person of ordinary skill in the art will have no difficulty in selecting the proper conditions, equipments and any other element for performing these steps.

Step f), which is essential for achieving the final product, is also a common step of crystallization that can be carried out by the normal chemistry practitioner, either on lab scale or in industrial scale, just selecting the proper conditions, such as volumes, temperatures, time.

Isolation of the polymorph Form II of 7-(dimethoxy-methyl)-camptothecin is carried out according to normal practice and this step need no further explanation.

Preferably, the final product is dried in order to eliminate solvent traces.

A further object of the present invention are solvates of the above polymorph Form II of 7-(dimethoxy-methyl)-camptothecin.

Camptothecin is a commercial product or can be prepared according to literature methods, see for example U.S. Pat. Nos. 5,053,512, 4,894,456, 5,405,963 and 6,982,333, Starting camptothecin is suspended into methanol (0.5 to 10%; preferably 1.5% solution w/v). The solution or suspension is kept at a temperature ranging from −10 to 80° C. (preferably 0 to 50° C.) and added with a mineral or organic acid, preferably $H_2SO_4$ 90 to 98% (preferably 96%) (1% to 30%, preferably 10% v/v), and at the presence of a suitable first oxidizing system (for example 30% $H_2O_2$/Fe(II) salts), then a second oxidizing agent (for example acetic acid, $CrO_3$, $MnO_2$) to obtain the desired product. A preferred first oxidizing system is iron sulphate/hydrogen peroxide. A preferred second oxidizing system is manganese dioxide.

The dried solid is then suspended in freshly distilled or with low water content methanol (30% solution) and a mineral or organic acid ranging between catalytic to stoichiometric amounts are added. The acid can be selected from the preferred group consisting of $H_2SO_4$, $CH_3COOH$, $H_3PO_4$, HCl $SOCl_2$, $COCl_2$, $CH_3SO_2OH$ (MsOH), $CH_3PhSO_2OH$ (TsOH), $CF_3COOH$, $CF_3SO_3H$. Other acids can be used with similar results. Preferred acid and its concentration are 10% v/v of $H_2SO_4$ 98%

After a suitable time, such as 2-6 h, the solution is neutralized until about pH 6 with a suitable base, such as aqueous NaOH, KOH or $Na_2CO_3$.

Then water is added to obtain a yellow precipitate which is isolated, preferably by filtration and crystallized again from MeOH.

The obtained solid is finally dried, for example under vacuum at 40° C. overnight.

The polymorph Form II is suitable as intermediate for the preparation of camptothecin derivatives, such as the ones disclosed in EP 0 056 692, in particular, and preferably the ones disclosed in WO03/101995 and any other camptothecin derivative for use as in the treatment of diseases responding to inhibition of Topoisomerase I, such as for example tumors, HIV infections and parasitic infections.

In an exemplary embodiment of the invention, the polymorph Form II of 7-(dimethoxy-methyl)-camptothecin was used as intermediate product for the preparation of the compounds disclosed in WO03/101995.

The following examples further illustrate the invention.

EXAMPLE 1

To a suspension of 1.53 g (4.4 mmol) of camptothecin in 92 ml of methanol, cooled with an ice bath under stirring, were added slowly 9.2 ml of $H_2SO_4$ 96%, keeping the temperature of the mixture below 50° C. The suspension thus obtained was heated to reflux temperature; on reaching 50° C., 46 mg of $FeSO_4$ $7H_2O$ were added and then 3 ml of $H_2O_2$ 30% drop-wise, keeping the reaction at reflux temperature. The reaction was stirred for 2 hours, checking for disappearance of the starting product by TLC. On completion of the reaction, the suspension was cooled to 25° C. and 2.8 g of $MnO_2$ were added; the mixture was stirred for 2 hours, checking for disappearance of the intermediate product by TLC. The suspension was then filtered through a layer of Celite placed on a Gooch filter.

The reaction mixture was concentrated under reduced pressure and the solid obtained was suspended in freshly distilled or low water content methanol and $H_2SO_4$ (98%) (4.4 equivalent).

The suspension was stirred for 6 h and then was neutralized until about pH 6 with 1N NaOH solution.

Then water was added to obtain a yellow precipitate which was isolated by filtration. The solid was crystallized from MeOH and dried under vacuum at 40° C. overnight.

Solid State Characterization of 7-(Dimethoxy-Methyl) Camptothecin (Form II)

X-Ray Powder Diffractometry

The X-ray powder diffractogram on about 15 mg of ground powder was obtained using a computer controlled XRD powder diffraction apparatus and examined under inert atmosphere.

The tube conditions were 40 KV×40 mA CuKα, the windows used were aperture 0.3°, and closing 0.15°. The time for each step scan was 7 s, the 2-θ range was 5°-35°.

After the acquisition, an accurate analysis of the spectrum was performed adopting a procedure for the peak evaluation taking into account both the minimum peak width and an estimated amount of disordered part. It is concluded that the sample is crystalline.

The characteristic main diffraction peaks are given in the following table 1.

TABLE 1

| Degrees 2-Theta ± 0.2 | Relative intensity (%) |
|---|---|
| 6.3 | 20 |
| 8.7 | 21 |
| 10.6 | 100 |
| 12.9 | 8 |
| 13.6 | 23 |
| 16.3 | 18 |
| 16.7 | 20 |
| 18.6 | 6 |
| 19.5 | 13 |
| 21.2 | 21 |
| 23.9 | 6 |
| 25.3 | 22 |
| 26.2 | 9 |
| 27.3 | 17 |
| 28.5 | 4 |
| 28.9 | 4 |
| 29.5 | 4 |
| 30.5 | 4 |
| 31.4 | 9 |
| 32.7 | 2 |

Figure 1:
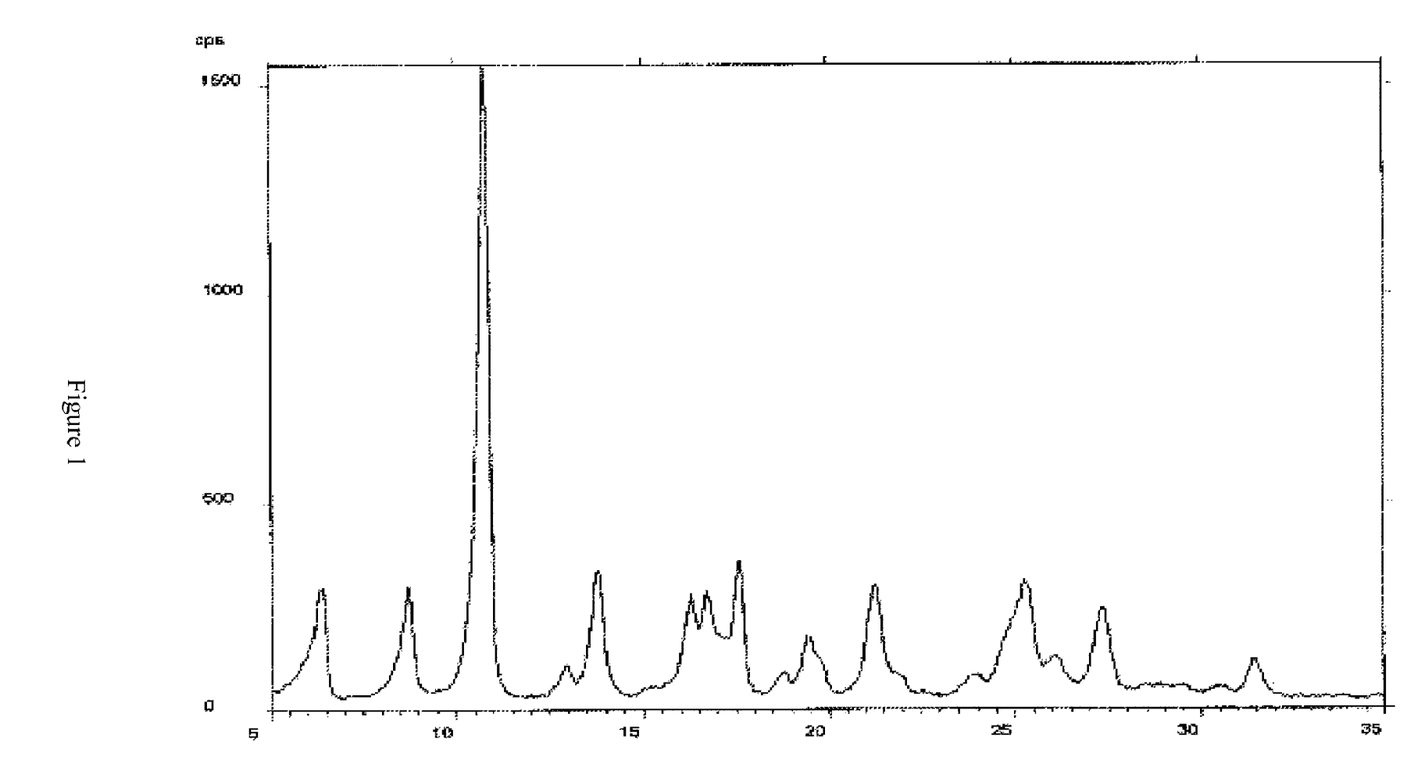
FIG. 1 represents the X-ray powder diffractogram of the polymorph Form II of the present invention, using a computer controlled XRD powder diffraction apparatus and examined under inert atmosphere. Diffractometry conditions were 40 KV×40 mA CuKα.

FIG. 1 shows X-ray powder diffractogram of 7-(dimethoxy-methyl)camptothecin (form II).

The most representative peaks are given in Table 2 below.

TABLE 2

| Degrees 2-Theta | Relative intensity (%) |
|---|---|
| 6.3 | 20 |
| 8.7 | 21 |
| 10.6 | 100 |
| 13.6 | 23 |
| 16.3 | 18 |
| 16.7 | 20 |
| 19.5 | 13 |
| 21.2 | 21 |
| 25.3 | 22 |
| 27.4 | 17 |

IR Spectrum

The diffuse reflectance FT-IR spectrum of 7-(dimethoxy-methyl)camptothecin form II was collected on a 2% sample in KBr with a Thermo Nicolet spectrometer model Avatar 370 DTGS.

In the following table 3 main signals (cm$^{-1}$) characteristic of this crystalline form are reported.

TABLE 3

| Frequency (cm$^{-1}$) | Intensity (% T) |
|---|---|
| 3518 | 53 |
| 2989 | 65 |
| 2936 | 65 |
| 1744 | 21 |
| 1660 | 21 |
| 1463 | 50 |
| 1155 | 31 |
| 1060 | 23 |
| 769 | 37 |

Figure 2:
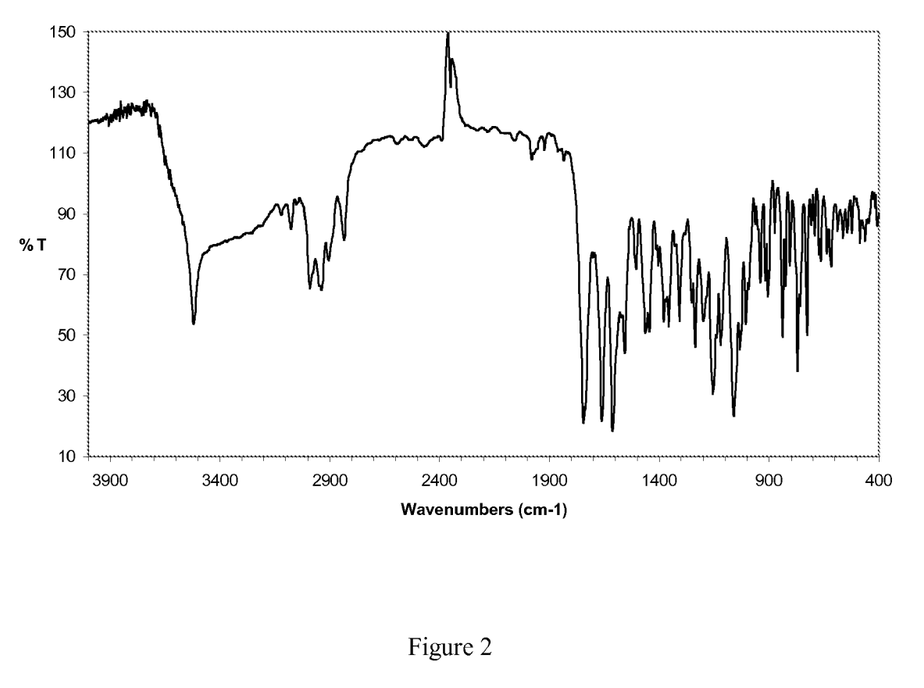
FIG. 2 represents the diffuse reflectance FT-IR spectrum of the compound of the present invention, the polymorph Form II, in KBr with a Thermo Nicolet spectrometer model Avatar 370 DTGS.

FIG. 2 shows IR Spectrum (in KBr) of 7-(dimethoxy-methyl)camptothecin (form II)

Figure 3:
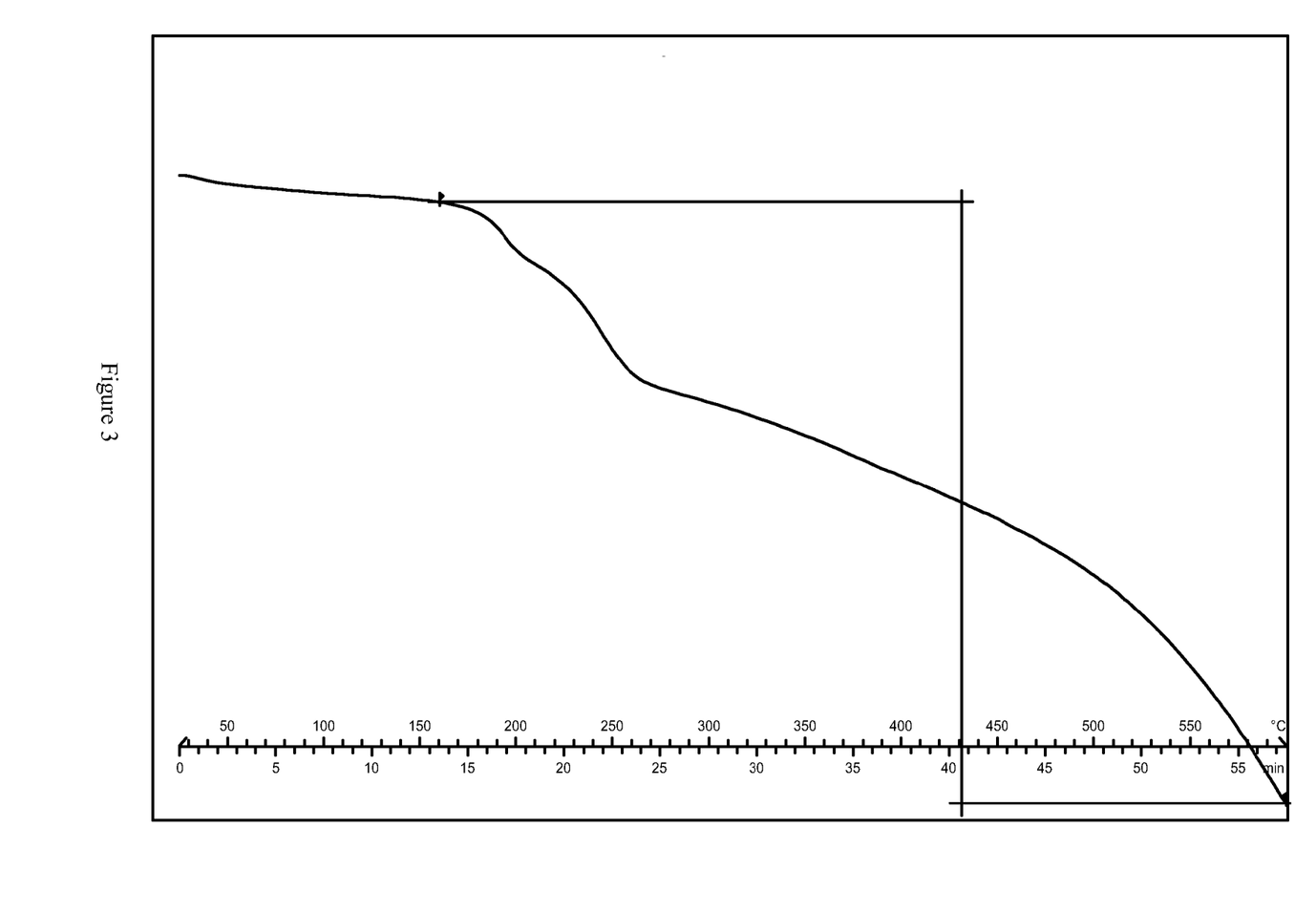
FIG. 3 represents thermal behaviour of the compound of the invention measured by a melting range apparatus.
Figure 4:
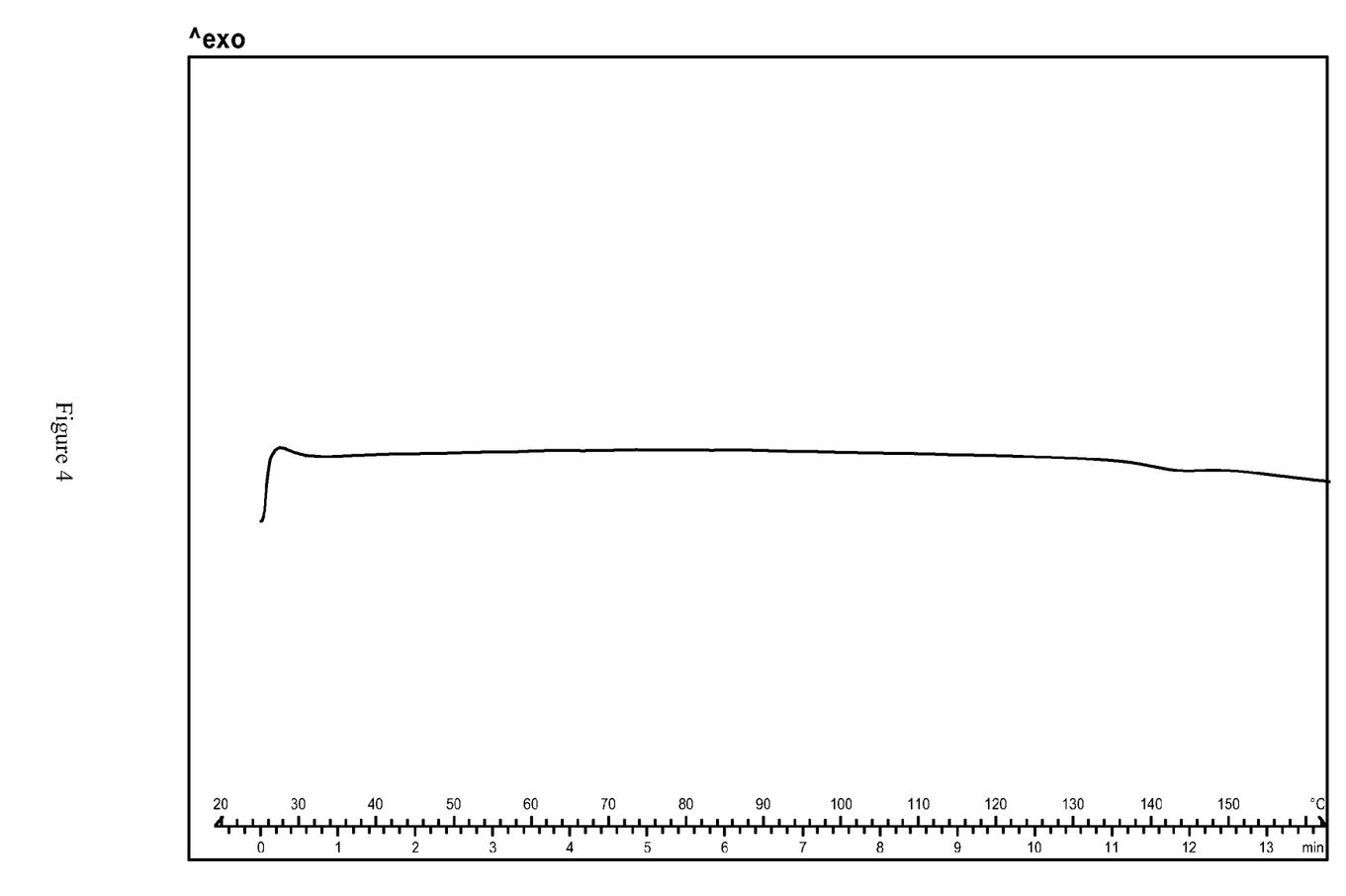
FIG. 4 represents differential scanning calorimetry (DSC) analysis of the polymorph Form II.
Figure 5:
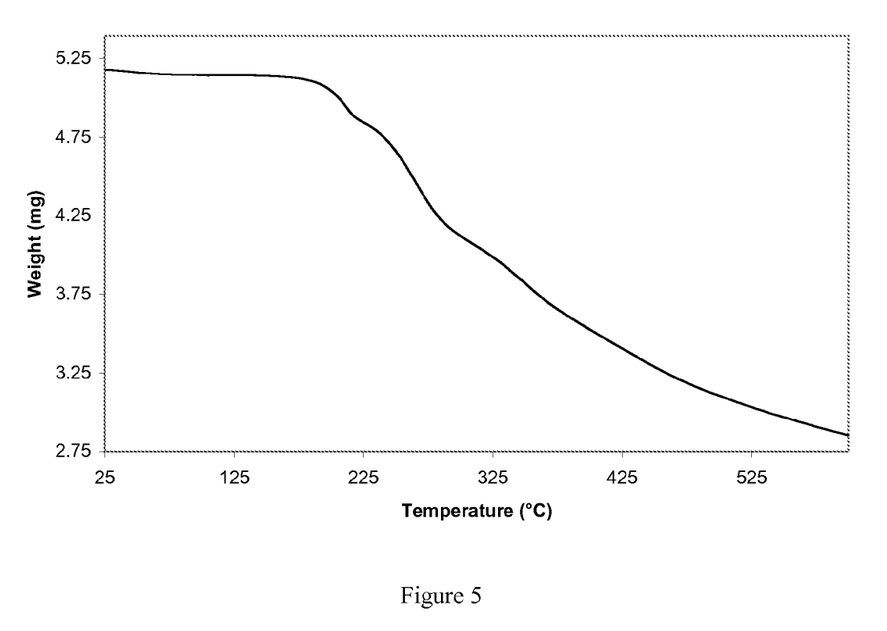
FIG. 5 represents differential scanning calorimetry (DSC) analysis of the polymorph Form II with a different scanning speed.
Figure 6:
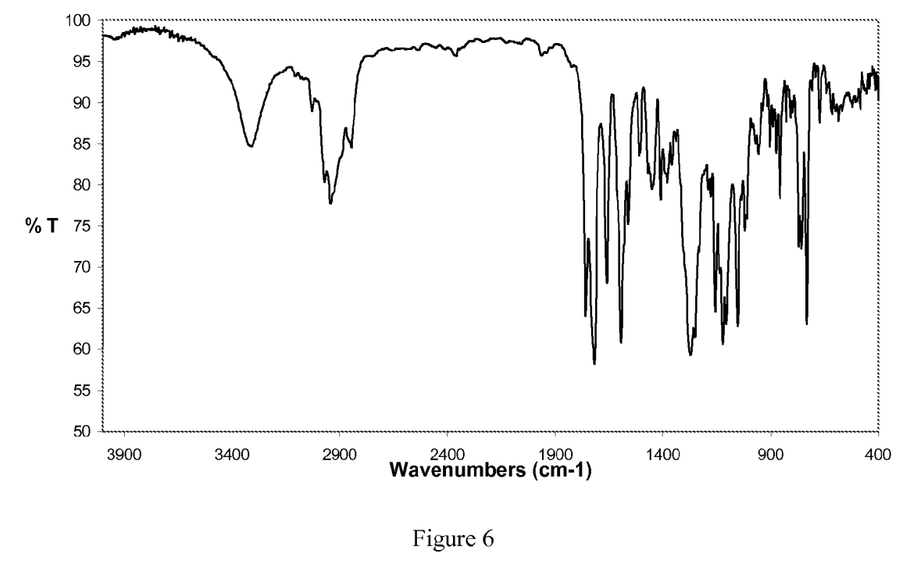
FIG. 6 shows FT-IR spectrum of 7-(dimethoxymethyl) camptothecin polymorph of the prior art (Form I).

Thermal Behaviour 7-(dimethoxy-methyl)camptothecin undergoes degradation starting from the temperature of about 160° C., measured by a suitable melting range apparatus (Mettler TG 50, temperature ramp from 25° C. to 600° C. at 10° C./min., see FIG. 3) and confirmed by the differential scanning calorimetry analysis (DSC mod. Mettler DSC 30, temperature ramp from 25° C. to 160° C. at 10° C./min., see FIG. 4) which indicates that no melting phenomena occurred before 160° C. The same experiment was repeated at different heat rump (20° C./min) giving a value of decomposition temperature at 173.56° C. (see FIG. 5).

HPLC-MS Analysis

An HPLC-MS analysis was performed in order to study the impurity profile of 7-(dimethoxy-methyl)camptothecin. In the following described experimental conditions no peak with a molecular weight compatible with aldehyde has been found.

Experimental Conditions:

Equipment:
  Surveyor LC, micro pump, Autosampler—Thermo;
  LCQ DecaXP Plus ion trap mass spectrometer with ESI (+) interface, Thermo;
Column:
  Inertsil ODS-3 (5 μm, 150×4.6 mm ID)—GL Sciences Inc.;
Mobile phase:
  A: H$_2$O+HCOOH 0.1%;
  B: H$_2$O/CH$_3$CN 10/90 v/v+HCOOH 0.1%;
Gradient elution:
  A/B 70/30 to 100% B in 20 minutes;
Flow rate:
  1.0 mL/min;
Detection:
  ESI (+) interface: capillary temp. 300° C.;
  Shield gas flow (N$_2$): 70;
  Auxiliary gas flow (N$_2$): 10;
  Capillary voltage: 3 V;
Source voltage:
  5 kV;
Source current:
  80 μA;
Tube lens offset:
  20 V;
Acquisition range:
  200-600 amu.

EXAMPLE 2

Comparative Example

This Example was conducted in order to ascertain the differences between the crystal form of the 7-(dimethoxy-methyl)camptothecin obtained by chloroform/n-hexane crystallization, as described by the above mentioned Sawada et al., 1994, and named herein Form I) and the 7-(dimethoxy-methyl)camptothecin obtained according to the present invention, named Form II.

The results (FT-IR, powder x-ray and TGA) showed the existence of differences between the two forms and that the form II is more stable (it decomposes at higher temperature) in comparison with the other form I.

The aim of this example is to verify that the form described in the cited article, crystallized by chloroform and n-hexane (named Form I), is different from Form II of the present invention.

Equipments

FT-IR Spectrophotometer THERMO (Nicolet 5700) connected to a PC via the OMNIC analysis software;

Drying oven;

Stirring Plate;

TGA thermobalance PerkinElmer (Analytical dept. Lab. MASC);

NMR Varian (Analytical dept. Lab. MASC);

Powder X-Ray (ISMAC).

Sample and Solvent 7-(dimethoxy-methyl)camptothecin: According to Example above.

n-hexane: MERCK (Batch K37503267 725) (Boiling Point 69° C.).

Chloroform: Sigma Aldrich (Batch 01635EC-344) (Boiling Point 61° C.).

The compound 7-(dimethoxy-methyl)camptothecin was prepared according to steps a)-e) described above and in Example 1.

Crystallisation Technique

About 130 mg of 7-(dimethoxy-methyl)camptothecin were solubilised in about 15 ml of chloroform, in a brown round bottom flask, under magnetic stirring. After complete solubilisation of the solid, the solution was filtered on Nalgene 0.2 µm filter, and then added with about 10 ml of n-hexane until to obtain complete precipitation.

The obtained crop was separated by filtration and dried with vacuum pump.

Characterization of 7-(Dimethoxy-Methyl)Camptothecin Form I

Figure 12:
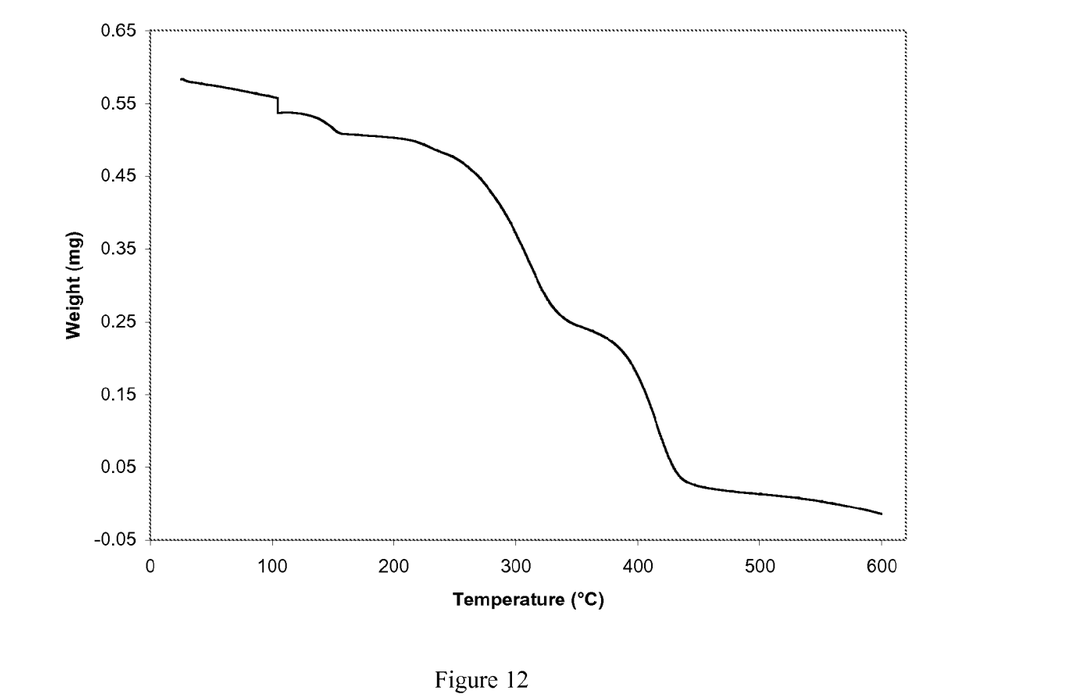
FIG. 12 shows thermal behaviour of 7-(dimethoxy-methyl) camptothecin form I.

The solid obtained was identified by NMR spectroscopy, using a NMR 500 spectrometer (solid solubilized in DMSO) and characterized by FT-IR (FIGS. 6, 7, 8 and 9), XRPD (FIG. 10) and TGA (FIG. 12).

The NMR is in compliance with the structure of 7-(dimethoxy-methyl)camptothecin.

Figure 7:
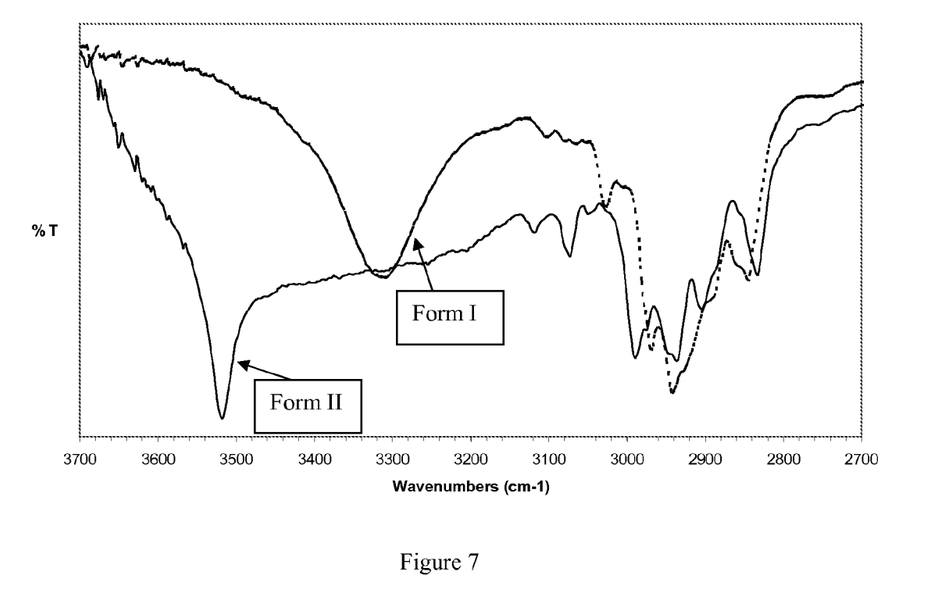
FIGS. 7-9 show compared FT-IR spectra of 7-(dimethoxymethyl)camptothecin polymorph according to the present invention (Form II) and of the prior art (Form I).
Figure 8:
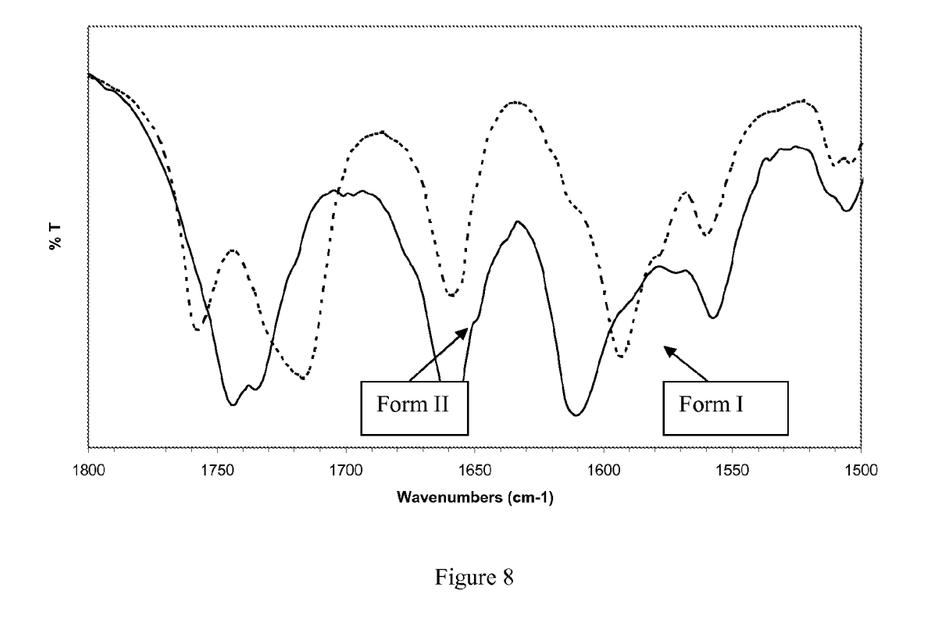
Figure 9:
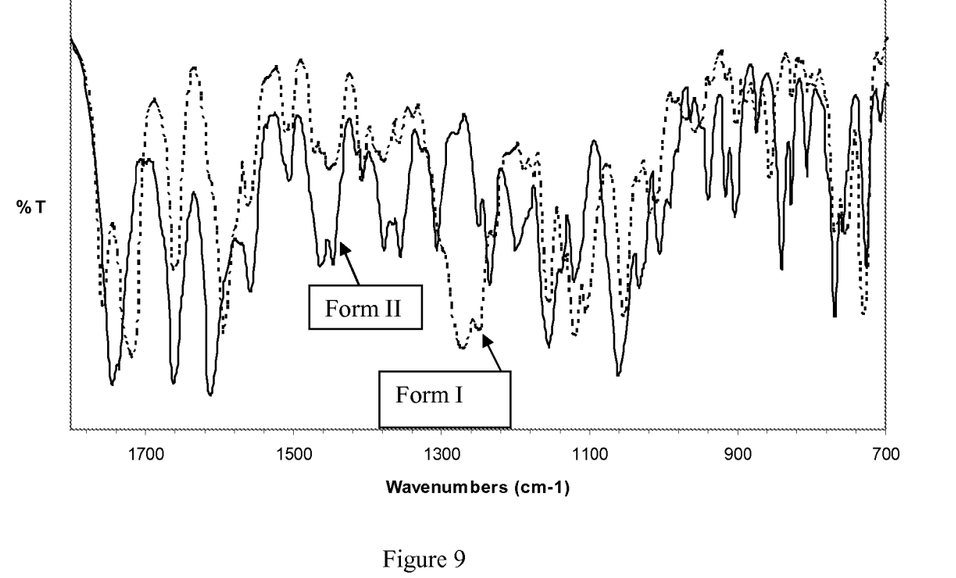
Figure 10:
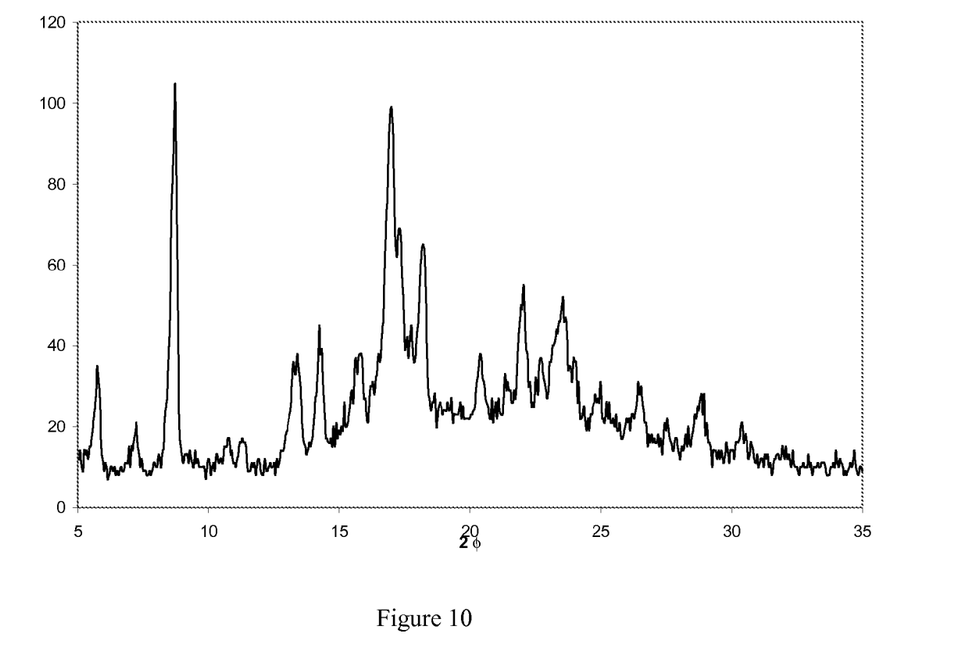
FIG. 10 shows X-ray powder diffractogram of the polymorph Form I of the prior art.

The comparison between infrared spectra of Form II and Form I showed a significant difference between the region 3600-2700 $cm^{-1}$, around 1700 $cm^{-1}$ and between 1600-800 $cm^{-1}$ (show FIGS. 7, 8 and 9).

The FT-IR Match between these two forms is 35.05%.

TABLE 4

2θ values of X-ray powder diffractogram for 7-(dimethoxy-methyl)camptothecin Form I

| Degrees 2-Theta | Relative intensity (%) |
| --- | --- |
| 5.75 | 33.65 |
| 7.25 | 20.19 |
| 8.75 | 100 |
| 13.4 | 36.53 |
| 14.25 | 43.26 |
| 14.9 | 20.19 |
| 15.2 | 25 |
| 15.65 | 35.57 |
| 15.85 | 36.53 |
| 17 | 95.19 |
| 17.3 | 66.34 |
| 17.75 | 43.26 |
| 18.2 | 62.5 |
| 20.4 | 36.53 |
| 22.05 | 52.88 |
| 22.7 | 35.57 |
| 23.55 | 50 |

TABLE 4-continued

2θ values of X-ray powder diffractogram for 7-(dimethoxy-methyl)camptothecin Form I

| Degrees 2-Theta | Relative intensity (%) |
| --- | --- |
| 26.45 | 29.80 |
| 28.95 | 26.92 |

Figure 11:
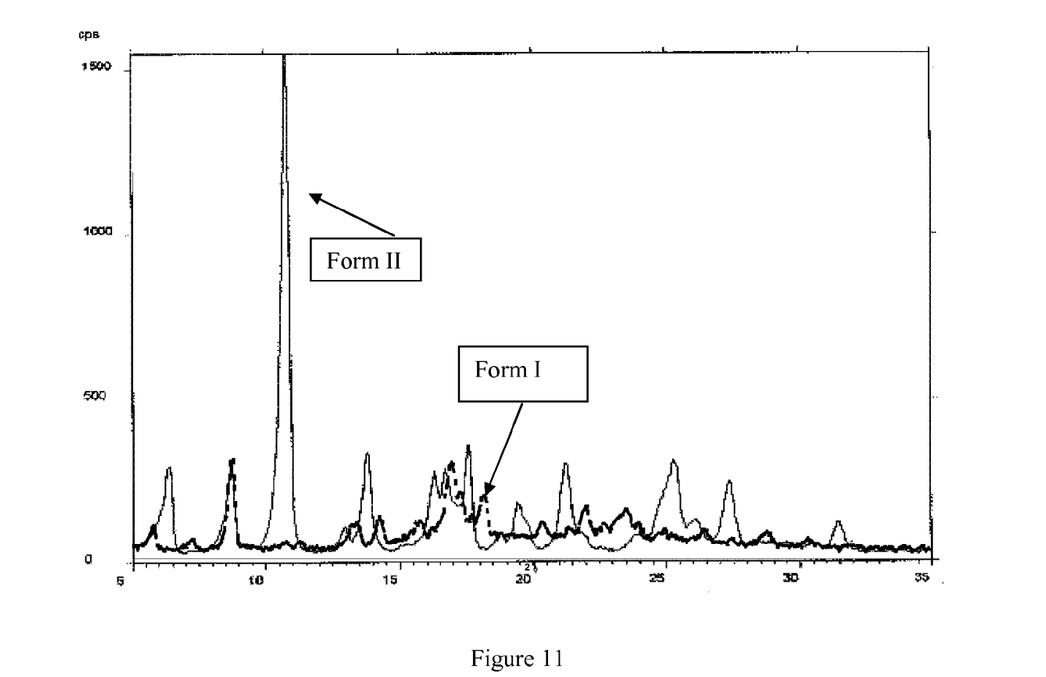
FIG. 11 shows the comparison between XRPD spectra of Form II, the 7-(dimethoxymethyl)camptothecin polymorph according to the present invention, and polymorph Form I of the state of the art.

The comparison between XRPD spectra of Form II and Form I showed a significant difference (see FIG. 11). In fact, the most characteristic diffraction peaks of Form II are at 6.3, 10.6, 19.5 and 25.3 degree (while those relatives of Form I are at 5.75, 18.2, and 23.55 degree).

Thermal Behaviour 7-(dimethoxy-methyl)camptothecin form I undergoes degradation starting from the temperature of 123.38° C. (the step around 100° C. is due to variation of heating ramp), measured by a suitable melting range apparatus (Mettler TG 50, temperature ramp from 25° C. to 600° C. at 20° C./min., see FIG. 12) and confirmed by the differential scanning calorimetry analysis (DSC mod. Mettler DSC 30, temperature ramp from 25° C. to 160° C. at 20° C./min.) which indicates that no melting phenomena occurred.

CONCLUSION

The study of crystal form of the 7-(dimethoxy-methyl) camptothecin obtained by chloroform/n-hexane (Form I) and Form II, showed significant differences between them.

The DSC-TGA analysis showed that this Form I is less stable in comparison with Form II, in fact the decomposition temperature of Form II is 173.56° C. while for the form I is 123.38° C.

Both solid forms of 7-(dimethoxy-methyl)camptothecin have almost thermal behaviour when the melting points were performed by a very similar instrument used by Sawada in 1991. In fact using a BUCHI 535 melting point we are not able to appreciate the decomposition and the melting phenomena can be confused with decomposition. With Buchi system we registered a melting point closed to 222-224° C. for form 1 and 224-226° C. for form II.

The invention claimed is:

1. Polymorph Form II of 7-(dimethoxy-methyl)camptothecin which undergoes degradation starting from the temperature of about 160° C., wherein said polymorph shows an X-ray powder diffraction pattern having the following characteristic peaks expressed in degrees 2Θ±0.2

| Degrees 2-Theta | Relative intensity (%) |
| --- | --- |
| 6.3 | 20 |
| 8.7 | 21 |
| 10.6 | 100 |
| 13.6 | 23 |
| 16.3 | 18 |
| 16.7 | 20 |
| 19.5 | 13 |
| 21.2 | 21 |
| 25.3 | 22 |
| 27.4 | 17. |

2. The polymorph Form II according to claim 1, which shows an X-ray powder diffraction pattern as shown in FIG. 1.

3. The polymorph Form II according to claim 1, which shows an IR spectrum (KBr) with the following main peaks:

| Frequency (cm$^{-1}$) | Intensity (% T) |
|---|---|
| 3518 | 53 |
| 2989 | 65 |
| 2936 | 65 |
| 1744 | 21 |
| 1660 | 21 |
| 1463 | 50 |
| 1155 | 31 |
| 1060 | 23 |
| 769 | 37. |

4. The polymorph Form II according to claim 1, which shows an IR spectrum as shown in FIG. 2.

5. The polymorph Form II according to claim 1, which is substantially free from aldehyde impurity.

6. A process for the preparation of the polymorph Form II of claim 1, comprising the following steps:
 a. oxidizing position 7 of camptothecin or a derivative thereof to obtain the corresponding 7-keto-camptothecin or 7-keto-camptothecin derivative;
 b. treating 7-keto-camptothecin or 7-keto-camptothecin derivative obtained in step a) with methanol, in the presence of an acid to obtain a first, acid methanol reaction mixture;
 c. neutralizing said first, acid methanol reaction mixture from step b) to obtain a second, substantially neutral methanol reaction mixture;
 d. adding water to said second, substantially neutral methanol reaction mixture, to obtain a precipitate;
 e. separating said precipitate of step d) to obtain an isolated precipitate;
 f. crystallizing said isolated precipitate of step e) from methanol to give said polymorph.

7. Process according to claim 6, wherein the oxidizing step of step a) is performed with a first oxidizing system and a second oxidizing system.

8. Process according to claim 7, wherein said first oxidizing system is 30% $H_2O_2$/Fe(II) salt and said second oxidizing system is selected from the group consisting of acetic acid, $CrO_3$, and $MnO_2$.

9. Process according to claim 8, wherein said first oxidizing system is 30% $H_2O_2$/iron sulphate and said second oxidizing system is manganese dioxide.

10. Process according to claim 6, wherein said first, acid methanol reaction mixture of step b) is selected from the group consisting of distilled methanol and 30% water/70% methanol solution.

11. Process according to claim 6, wherein said acid of step b is selected from the group consisting of $H_2SO_4$, $CH_3COOH$, $H_3PO_4$, HCl $SOCl_2$, $COCl_2$, $CH_3SO_2OH$, $CH_3PhSO_2OH$, $CF_3COOH$, $CF_3SO_3H$.

12. Process according to claim 11, wherein said acid of step b) is 98% $H_2SO_4$.

13. Process according to claim 11, wherein said acid is in a concentration of 10% v/v.

14. Process according to claim 6, wherein, after step f) said crystallized polymorph Form II is dried under vacuum at 40° C. overnight.

15. Process for the preparation of a camptothecin derivative with the polymorph Form II of claim 1.

* * * * *